United States Patent [19]

Ayad

[11] Patent Number: 4,798,839

[45] Date of Patent: Jan. 17, 1989

[54] SYNERGISTIC INSECTICIDAL COMPOSITIONS

[75] Inventor: Hafez M. Ayad, Cary, N.C.

[73] Assignee: Rhone Poulenc Nederlands B.V., Amstelveen, Netherlands

[21] Appl. No.: 586,961

[22] Filed: Mar. 7, 1984

Related U.S. Application Data

[63] Continuation-in-part of Ser. No. 363,830, Mar. 31, 1982, abandoned.

[51] Int. Cl.$^4$ .................. A01N 37/34; A01N 43/30; A01N 43/46; A01N 47/28
[52] U.S. Cl. .................... 514/351; 514/348; 514/349; 514/464; 514/521; 514/522; 514/594
[58] Field of Search ............ 424/263; 514/351

[56] References Cited

U.S. PATENT DOCUMENTS

| | | | |
|---|---|---|---|
| 3,748,356 | 7/1973 | Wellinga et al. | 260/553 E |
| 3,922,242 | 11/1975 | Henry | 424/263 |
| 4,172,135 | 10/1979 | Kristiensen et al. | 424/263 |
| 4,173,637 | 11/1979 | Nishiyama et al. | 424/263 |
| 4,275,060 | 6/1981 | Geering | 424/282 |
| 4,310,694 | 1/1982 | Ehrenfreund | 424/322 |
| 4,323,579 | 4/1982 | Ehrenfreund | 564/44 |
| 4,390,715 | 6/1983 | Holan et al. | 424/282 |

FOREIGN PATENT DOCUMENTS

| | | | |
|---|---|---|---|
| 1124242 | 5/1982 | Canada. | |
| 0040179 | 11/1981 | European Pat. Off. | 424/263 |

OTHER PUBLICATIONS

Wilkinson et al. Journal of Ag. & Food Chemistry, vol. 14, No. 1, Jan.–Feb. 1966, pp. 73–79.
Georghiou et al., Journal of Ag. Research 3(1):31–35, (1964).

*Primary Examiner*—Allen J. Robinson
*Attorney, Agent, or Firm*—Morgan & Finnegan

[57] ABSTRACT

Insecticidal compositions are provided which contain mixtures of certain benzoyl ureas and a synergist which is a methylenedioxyphenyl derivative. The invention also encompasses a method of controlling insects by subjecting them to an effective amount of the synergistic insecticidal compositions.

2 Claims, No Drawings

SYNERGISTIC INSECTICIDAL COMPOSITIONS

This application is a continuation-in-part of prior U.S. application Ser. No. 363,830 (now abandoned) filed Mar. 31, 1982.

FIELD OF THE INVENTION

This invention relates, in general, to synergistic insecticidal compositions. In one aspect, this invention relates to compositions which contain certain benzoyl ureas in admixture with a methylenedioxyphenyl derivative, such as piperonyl butoxide. In a further aspect, this invention relates to a method of controlling insects by the application of insecticidally effective amounts of mixtures of benzoyl ureas and piperonyl butoxide.

BACKGROUND OF THE INVENTION

Insecticide synergists are compounds which, although having no direct toxic effect at the dosage employed, are able to substantially enhance the observed toxicity of an insecticide with which they are combined. For example, Wilkinson, Metcalf, and Fukuto, *Journal of Agricultural and Food Chemistry*, Volume 14, No. 1, pages 73–79 1966, found that certain methylenedioxyphenyl compounds gave synergistic kill of the common house fly when combined with 1-naphthyl N-methylcarbamate, 3,4-dimethoxyphenyl N-methylcarbamate, and 4-di-methylamino-3,5-xylenyl N-methylcarbamate.

Georghiou and Atkins, Jr., *Journal of Agricultural Research*, Volume 3, No. 1, pages 31–35 1964, demonstrated that piperonyl butoxide increased the toxity of SEVEN, Zectran and B 37344 (4-methylthio-3,5-xylyl N-methylcarbamate) to honeybees (*Apis mellifera*).

Although the aforementioned referencesindicate that a synergistic effect is obtained when certain compounds are combined with specific known insecticides, there is no broad teaching that such compounds would have the same effect when mixed with other insecticides.

For example, U.S. Pat. Nos. 4,173,637 and 3,748,356 disclose that the mixtures of the compounds described in these two patents with other insecticides, miticides and plant growth regulators sometimes produce synergistic effects. However it has been observed that mixtures containing Dimilin or N-(2-chlorobenzoyl)-N'-[4(3,5-dibromopyridyl-2-oxy)phenyl]urea, two compounds described in U.S. Pat. Nos. 3,748,356 and 4,173,637, respectively, and piperonyl butoxide do not produce synergistic kill of many insects, such as the armyworm.

Moreover, to attempt to determine which synergist would be effective with which insecticide by a trial and error technique is beyond the economic capability of most research laboratories. Hence, it was indeed unexpected and surprising to find that methylenedioxyphenyl derivatives were effective synergists when employed in admixture with certain benzoyl urea insecticides. Thus, according to the present invention it was found that the amount of benzoyl urea insecticide can be greatly reduced resulting not only in economic savings but more importantly protecting the natural environment as well.

Accordingly, one or more of the following objects can be achieved by the practice of this invention. It is an object of this invention to provide novel insecticidal compositions which contain mixtures of a synergist and certain benzoyl ureas. Another object of this invention is to provide insecticidal compositions containing mixtures of piperonyl butoxide and cerain benzoyl ureas. A further object is to provide insecticidal compositions wherein the active toxicant can be employed in a reduced amount and still achieve the desired insect control. A still further object of the invention is to provide a method for controlling insect growth by the application of the composition of this invention. Those and other objects will readily become apparent to those skilled in the art in the light of the teachings herein set forth

DETAILED DESCRIPTION OF THE INVENTION

In its broad aspect, the invention is directed to synergistic insecticidal compositions and to a method for their use. As indicated above, the synergistic insecticidal compositions of this invention are comprised of a mixture of a benzoyl urea and a methylenedioxyphenyl derivative.

The benzoyl urea component of the compositions of this invention encompasses compounds of the general structure:

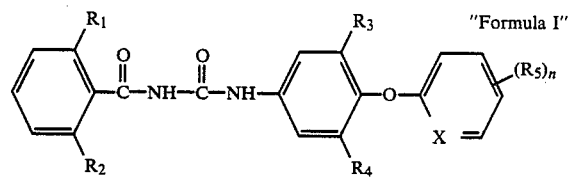

"Formula I"

wherein $R_1$ and $R_2$ individually represent hydrogen, chloro, fluoro, or alkyl and alkoxy of up to 10 carbon atoms; $R_3$ and $R_4$ individually represent hydrogen, chloro or trifluoromethyl; $R_5$ represents individually halo, nitro, cyano, or trifluoromethyl; n is 1 or 2; and X represents carbon or nitrogen with the proviso that at least one of $R_3$ and $R_4$ must be chloro or trifluoromethyl.

Preferred compounds are those of the above formula wherein $R_1$ is chloro or fluoro, $R_2$ is hydrogen or fluoro, $R_3$ and $R_4$ are both chloro, $R_5$ is 3-chloro-5-trifluoromethyl and X is nitrogen. When X is carbon, $R_5$ may be also 4-nitro.

Illustrative benzoyl ureas are compounds such as, 4-nitro-2',6'-dichloro-4'-[N-(N'-2,6-difluorobenzoyl-)ureido]-diphenyl ether, 4-nitro-2',6'-dichloro-4'-[N-(N'-2-fluorobenzoylureido]-diphenyl ether, 4-nitro-2',6'-dichloro-4'-[N-(N'-2-methylbenzoyl-)ureido]-diphenyl ether, 4-nitro-2',6'-dichloro-4'-[N'-2,6-dichlorobenzoyl-)ureido]-diphenyl ether, N-(2,6-difluorobenzoyl)-N'-[3,5-dichloro-4-(5-trifluoromethylpyridyl-2-oxy)phenyl]urea, N-(2,6-difluorobenzoyl)-N'-[3,5-dichloro-4(3-chloro-5-trifluoromethylpyridyl-2-oxy)phenyl]urea, N-(2,6-difluorobenzoyl)-N'-[3-chloro-4-(3-chloro-5-trifluoromethylpyridyl-2-oxy)phenyl]urea, The benzoyl ureas employed in this invention are prepared by one or more procedures disclosed in the literature. For example, the 4-nitro-4'-[N-(N'-benzoyl-)ureido]diphenyl ethers are prepared either by reacting a nitro-phenoxyaniline with a benzoyl isocyanate or by reacting a 4-isocyanate-diphenyl ether with a benzamide. Further details for the preparation of the nitro diphenyl ether derivatives are set forth in U.S. Pat. No. 4,041,177 which is incorporated by reference.

Benzyl ureas wherein X in the above formulas is nitrogen can be prepared by the methods disclosed in U.S. Pat. No. 4,173,637 which is also incorporated by reference. For example, a benzoyl isocyanate can be reacted with a pyridyloxyaniline or a benzamide can be reacted with a pyridyloxyphenyl isocyanate.

The second component of the synergistic insecticidal compositions of this invention is a methylenedioxyphenyl derivative. The synergists are selected from the group consisting of:
alpha-[2-(2-butoxyethoxy)ethoxy]-4,5-methylenedioxy-2-propyltoluene (piperonyl butoxide);
piperonal bis-[2-(2-butoxyethoxy)ethyl]acetal (pipotal); 2-(2-ethyoxethoxy)ethyl-3,4-(methylenedioxy)-phenyl acetal of acetaldehyde (sesamex); and 1,2-methylenedioxy-4-[2-(octylsulfinyl)propyl]benzene (sulphoxide).

The preferred synergist is piperonyl butoxide.

The proportion of the benzoyl urea to the synergist can vary over a wide range depending on such factors as the particular locus to be treated, the particular pest to be combatted and the particular effect desired. The weight proportion of the benzoyl urea to the synergist may be, for example, from 1:0.05 to 1:3000, respectively. Usually there is a greater proportion of synergist than the benzoyl urea. Preferably, the proportion of benzoyl urea to synergist are from 1:170 to 1:2650 respectively.

In the preparation of the novel compositions of the present invention, the methylenedioxyphenyl compound is mixed with the benzoyl urea and a suitable inert carrier as hereinafter defined. One suitable method of preparing the compositions of the present invention is to mix piperonyl butoxide with or without solvent or diluent, with a suitable carrier and then mix the resulting composition with the benzoyl urea with or without solvent.

The synergist insecticidal compositions contemplated in this invention may be applied as insecticides according to methods known to those skilled in the art. These compositions will typically include conventional pest control adjuvants, diluents, modifiers or conditioning agents, herein included in the term "suitable carrier substance", to provide compositions in the form of solution, emulsions, dispersions, powders, dust, granules, pellets and the like. Thus, the insecticidal compositions can contain one or more surface active agents as a conditioning agent to render the composition readily dispersable in water. The term surface active agent includes wetting agents, dispersing agents, emulsifying agent and the like. The solid forumlations of the present invention in the form of powder, dust, pellets or granules can be prepared using such substances as talc, natural clay, pyrophyllite, diatomaceous earth, walnut shells, corn cobs, sugars, and the like.

Suitable liquid diluents or carriers include water, petroleum distillates, or other liquid carriers with or without surface active agents. Liquid concentrates may be prepared by dissolving one of these compositions with a non-phytotoxic solvent such as acetone, xylene, or nitro-benzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents, for example, the condensation products of alkylene oxides with phenol and organic acids, alkyl aryl sulfonates, complex ether alcohols, quaternary ammonium compounds, and the like may be employed for this purpose.

In the preparation of wettable powder or dust or granulated compositions, the active ingredient is dispersed in and on an appropriately divided solid carrier such as natural clay, talc, pyrophyllite, bentonite, diatomaceous earth, fullers earth, corn cobs, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about B 10 to 95 percent by weight and in the solid formulations from about 0.5 to about 90 percent by weight. Satisfactory sprays, dust, or granules for general use contain from about ¼ to 15 pounds of active toxicant per acre.

The insecticides contemplated herein prevent attachment by insects upon plants or other material to which the insecticides are applied. With respect to plants, they have a high margin of safety in that when used in sufficient amount to kill or repel the insects, they do not burn or injure the plant, and they resists weathering which includes wash-off caused by rain, decomposition by ultra-violet light, oxidation, or hydrolysis in the presence of moisture or, at least, such decomposition, oxidation, and hydrolysis as would materially decrease the desirable insecticidal characteristics of the toxicants or impart undesirable characteristics, for instance, phototoxicity, to the toxicants. The toxicants are compatible with other constituents of the spray schedule, and they may be used in the soil, upon the seeds, or the roots of plants. Mixtures of the synergistic insecticidal compositions of this invention may be employed if desired as well as combinations of the synergistic insecticidal compositions with one or more fungicides, bactericides, acaricides, nematocides, insecticides or other biologically active compounds.

The synergistic insecticidal compositions of this invention are effective against a wide variety of insects. It is understood that the Southern armyworm evaluated in the working Examples herein is representative of a wider variety of insect which can be controlled by the synergistic insecticidal compositions of this invention. These compositions are particularly useful in controlling insects of agricultural crops, e.g., potatoes, maize, sugar beets, cotton, rice, wheat, tobacco, soybeans, deciduous and citrus fruits.

The following examples illustrate the best mode presently contemplated for the practice of this invention:

EXAMPLE 1

Synergistic mixture of N-(2,6 difluorobenzoyl)-N'-[3,5-dichloro-4-(3-chloro-5-trifluoromethylpyridyl-2-oxy)phenyl]urea and piperonyl butoxide for control of Southern army worm larvae (*Spodeptora eridania* (Crammer)).

An aqueous suspension of the benzoyl urea and piperonyl butoxide were prepared by dissolving 0.1 grams of each compound in 10 milliliters of acetone in which had been dissolved 0.05 milliliters of an alkylphenoxy polyethyoxyethenol surfactant as an emulsifying or dispersing agent. The resulting solution was mixed with 90 milliliters of water to give 100 milliliters of a suspension containing each test compound in finely divided form. The thus prepared stock suspension contained 0.1 percent by weight of each compound. Potted tender green bean plants of standard height and age were placed on a revolving turntable and sprayed with 100–110 milliliters of test compound formulation by use of a De Vilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter petri dish lined with moistened filter paper. Five randomly selected larvae were introduced into each dish and the dishes were closed. The closed dishes were labeled and held at 80–85 F. and 50–55 percent relative humidity for three days. Although the larvae could easily consume the whole leaf within twenty-four hours, no more food was added. Larvae which were unable to move the length of the body, even upon stimulation by prodding, were considered dead. Percent mortality was recorded for various concentration levels.

The concentration employed in the test results presented below were obtained by diluting the stock suspensions with water. Dilution tests were conducted to determine the $LD_{50}$ (concentration required to kill 50 percent of armyworm larvae). The results of these tests are set forth in Table 1 below:

TABLE I
TOXICITY TO ARMYWORM LARVAE

| | | % Mortality | | |
|---|---|---|---|---|
| Pesticide | Concentration in ppm | Pesticide alone | 500 ppm synergist alone | Pesticide + 500 ppm synergist |
| N—(2,6 difluorobenzoyl)-N'—[3,5-dichloro-4-(3-chloro-5-trifluoromethyl-pyridyl-2-oxy)phenyl]urea | 3 | 85 | 0.0 | 100 |
| | 1.5 | 60 | | 95 |
| | 0.75 | 56 | | 85 |
| | 0.38 | 0 | | 67 |
| | 0.19 | — | | 35 |

EXAMPLE 2

Synergistic Mixture of 1-[3,5-dichloro-4-(4-nitrophenoxy)phenyl]-3-(2-chlorobenzoyl)urea and Piperonyl Butoxide.

In a manner identical to that employed in Example 1 a suspension of the benzoylurea and piperonyl butoxide was prepared and the concentrations set forth in Table II obtained by diluting the stock suspension with water. Application of the suspension to the green bean plants resulted in the indicated mortality of the armyworm larvae.

TABLE II
TOXICITY TO ARMYWORM LARVAE

| | | % Mortality | | |
|---|---|---|---|---|
| Pesticide | Concentration in ppm | Pesticide alone | 500 ppm synergist alone | Pesticide + 500 ppm synergist |
| 1-[3,5-dichloro-4-(4-nitrophenoxy)-phenyl]-3-(2-chlorobenzoyl) urea | 1.5 | 59 | 0.0 | 90 |
| | 0.75 | 40 | | 80 |
| | 0.38 | 27 | | 40 |

EXAMPLE 3

Mixture of N-(2-chlorobenzoyl)-N'-[4-(3,5-dibromopyridyl-2-oxy)-phenyl]urea and Piperonyl Butoxide In order to demonstrate that the synergistic effect is selective and not obtained when piperonyl butoxide is admixed with all benzoylureas of the type disclosed in U.S. Pat. No. 4,173,637, aqueous suspension were prepared of N-(2-chlorobenzoyl)-N'-[4-(3,5-dibromopyridyl-2-oxy)phenyl]urea and piperonyl butoxide by the same procedure of Examples 1 and 2. Application of the suspension to the green bean plant at the indicated concentration resulted in the mortality set forth in Table III below:

TABLE III
TOXICITY TO ARMYWORM LARVAE

| | | % Mortality | | |
|---|---|---|---|---|
| Pesticide | Concentration in ppm | Pesticide alone | 500 ppm synergist alone | Pesticide + 500 ppm synergist |
| N—(2-chlorobenzoyl)-N'—[4-(3,5-dibromopyridyl-2-oxy)phenyl] urea. | 20 | 90 | 0.0 | 75 |
| | 10 | 80 | | 67 |
| | 5 | 70 | | 17 |
| | 2.5 | 40 | | 5 |
| | 1.25 | 6 | | 0 |

EXAMPLE 4

Mixture of Dimilin* and Piperonyl Butoxide

In a manner similar to that employed in the previous examples, piperonyl was admixed with the composition disclosed in U.S. Pat. No. 3,748,356 in an aqueous solution and applied to the green bean plants at the concentrations indicated. The concentrations employed and the mortality are set forth in Table IV below:

TABLE IV
TOXICITY TO ARMYWORM LARVAE

| | | % Mortality | | |
|---|---|---|---|---|
| Pesticide | Concentration in ppm | Pesticide alone | 500 ppm synergist alone | Pesticide + 500 ppm synergist |
| Dimilin* | 60 | 80 | 0.0 | 90 |
| | 30 | 50 | | 63 |
| | 15 | 18 | | 22 |
| | 7.5 | 15 | | 15 |
| | 3.8 | 10 | | 0 |

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:
1. A synergistic insecticidal composition comprising:
   (1) an effective amount of a substituted benzoyl urea compound which is N-(2,6-difluorobenzyl)-N'-[3,5-dichloro-4-(3-chloro-5-trifluoromethylpyridyl-2-oxy)phenyl]urea; and,
   (2) an effective amount of a methylenedioxyphenyl compound which is alpha-[2-(2-butoxyethoxy)ethoxy]-4,5-methylenedioxy-2-propyltoluene wherein the weight proportion ratio of the substituted benzoyl urea compound to the methylenedioxyphenyl compound is from about 1:0.05 to about 1:3000 parts by weight respectively.

2. A method of controlling insects which comprises subjecting them to an effective amount of a synergistic insecticidal composition of claim 1.